(12) United States Patent
Wabel

(10) Patent No.: US 12,161,789 B2
(45) Date of Patent: Dec. 10, 2024

(54) DIALYSIS MACHINE

(71) Applicant: Fresenius Medical Care Deutschland GmbH, Bad Homburg (DE)

(72) Inventor: Peter Wabel, Rosbach (DE)

(73) Assignee: PRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 1051 days.

(21) Appl. No.: 16/971,402

(22) PCT Filed: Feb. 14, 2019

(86) PCT No.: PCT/EP2019/053671
§ 371 (c)(1),
(2) Date: Aug. 20, 2020

(87) PCT Pub. No.: WO2019/162184
PCT Pub. Date: Aug. 29, 2019

(65) Prior Publication Data
US 2020/0390956 A1 Dec. 17, 2020

(30) Foreign Application Priority Data
Feb. 21, 2018 (DE) .......................... 102018103936.0

(51) Int. Cl.
*A61M 1/28* (2006.01)
*A61M 1/16* (2006.01)
*A61M 39/10* (2006.01)

(52) U.S. Cl.
CPC ............ *A61M 1/28* (2013.01); *A61M 1/1672* (2014.02); *A61M 1/1674* (2014.02); *A61M 39/10* (2013.01); *A61M 2202/0486* (2013.01)

(58) Field of Classification Search
CPC .............................................. A61M 1/28–288
See application file for complete search history.

(56) References Cited

U.S. PATENT DOCUMENTS

| | | |
|---|---|---|
| 5,591,344 A | 7/1997 | Kenley et al. |
| 5,716,531 A | 2/1998 | Kenley et al. |
| 2012/0227484 A1 | 9/2012 | Chen et al. |
| 2013/0126430 A1 | 5/2013 | Kenley et al. |
| 2014/0276373 A1 | 9/2014 | Minkus |
| 2015/0005699 A1 | 1/2015 | Burbank et al. |
| 2016/0317733 A1 | 11/2016 | Fulkerson et al. |

(Continued)

FOREIGN PATENT DOCUMENTS

| | | |
|---|---|---|
| EP | 2871164 | 5/2015 |
| EP | 3222306 | 9/2017 |
| WO | WO2013/141896 | 9/2013 |

*Primary Examiner* — Kami A Bosworth
(74) *Attorney, Agent, or Firm* — Jacobson Holman PLLC

(57) ABSTRACT

The present invention relates to a dialysis machine, in particular to a peritoneal dialysis machine, having a device for preparing dialysis solution, wherein the device has an RO system equipped with a filter for the provision of RO water and has a mixing device that is configured to mix a dialysis concentrate with the RO water or with a solution containing RO water; wherein a control device is provided that is configured to operate the RO system continuously; and wherein a storage container is provided that is connected downstream of the RO system and that is configured to store the water generated in the RO system.

21 Claims, 1 Drawing Sheet

(56) References Cited

U.S. PATENT DOCUMENTS

Figure 1:
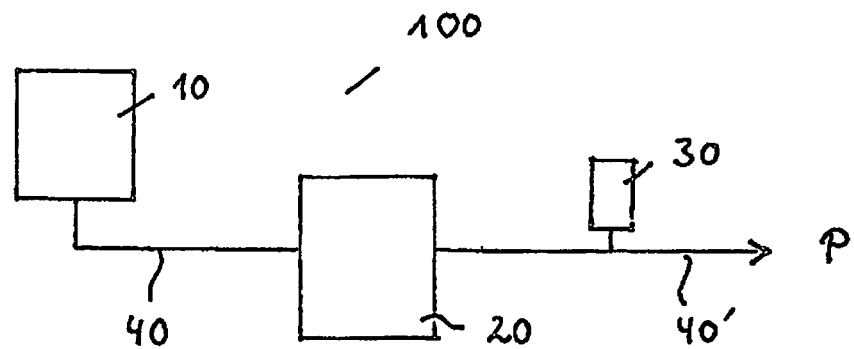

2017/0281845 A1   10/2017  Manda et al.
2017/0281846 A1   10/2017  Manda et al.
2017/0319770 A1*  11/2017  Fitzgerald ................. C02F 9/00

* cited by examiner

DIALYSIS MACHINE

The present invention relates to a dialysis machine, in particular to a peritoneal dialysis machine.

It is in particular customary in the field of peritoneal dialysis ("PD") to provide the patient with solution bags that are filled with a dialysis solution suitable for the patient. The patient typically connects these solution bags to an inflow hose, i.e. to the patient catheter, independently or with the aid of trained medical personnel to fill the peritoneum with the dialysis solution. The dialysis solution typically has to be transported to the house of the patient in a fully prepared state, which can bring about logistical problems that can emanate from the transportation of the bags to the patient and from the storage of the bags at the patient's.

It is the underlying object of the present invention to provide a dialysis machine, in particular a peritoneal dialysis machine, by means of which said logistical problems can be overcome.

This object is achieved by a dialysis machine, in particular by a peritoneal dialysis machine, having a device for preparing dialysis solution, wherein the device has an RO system equipped with a filter for the provision of RO water and has a mixing device that is configured to mix a dialysis concentrate with the RO water or with a solution containing RO water, wherein a control device is provided that is configured to operate the RO system continuously, and wherein a storage container is provided that is connected downstream of the RO system and that is configured to store the water generated in the RO system.

Provision is accordingly made that the dialysis machine has a device for preparing dialysis solution so that the delivery and storage of bags containing the dialysis solution can be omitted. It is rather sufficient to provide the patient with the concentrate or concentrates that are required for preparing the ready-to-use dialysis solution.

Said device for preparing the dialysis solution has an RO system equipped with a filter for providing RO water and has a mixing device that is configured to mix a dialysis concentrate with the RO water or with a solution containing RO water. The dialysis solution, in particular the peritoneal dialysis solution, is thus prepared at the dialysis machine itself by mixing RO water with one concentrate or with a plurality of concentrates. RO water can be mixed with one or more concentrates in the mixing device.

The RO system is preferably an integral component of the dialysis machine, but can also be designed as a separate unit that is in fluid communication with the dialysis machine so that the prepared RO water reaches the dialysis machine.

It is also conceivable that RO water is mixed with one or more concentrates in the mixing device or that a solution containing RO water, but not solely consisting of RO water, is mixed with one or more concentrates. This solution containing RO water can, for example, contain one or more ingredients such as electrolytes, an osmotic agent, etc. that had already been added to the RO water before further ingredients or concentrates are added to prepare the ready-to-use dialysis solution.

"RO water" is understood as that water that is e.g. acquired from mains water through reverse osmosis (RO), i.e. by the operation of the RO system.

Provision is furthermore made in accordance with the invention that the dialysis machine has a control device that is configured to operate the RO system continuously. The continuous operation of the RO system, i.e. the continuous supply of water to the RO system and/or the continuous draining of RO water from the RO system prevents a clogging or a contamination or a microbial contamination of the filter. What is important is that the filter of the RO system is flowed through continuously.

A storage container is furthermore provided that is connected downstream of the RO system and that is configured to store the water generated in the RO system. The storage container takes up the water generated in the RO system and prevents the RO water from having to be discarded, or delays the discarding in this manner, if no dialysis solution is required. This is only necessary when no dialysis treatment is carried out for a longer period and the storage container is full. A discarding of RO water can be prevented or at least reduced to a minimum by a suitable dimensioning of the storage container.

The storage container preferably has a volume such that at least one complete peritoneal dialysis treatment having a plurality of inflows can be carried out.

Not only the advantage that the use of dialysis solution bags can be dispensed with is achieved by the present invention, but also the advantage that the probability of a microbial contamination or other contamination of the RO system due to its long-term operation can be reduced with respect to an intermittent operation.

The term "continuous operation" is not necessarily to be understood such that the RO system is in operation permanently, i.e. twenty-four hours a day, even though this is likewise a conceivable embodiment of the invention. The term "continuous operation" is to be understood such that the RO system is at least also in operation when no dialysis treatment is taking place or when no dialysis solution is required or prepared.

The storage container can be connected upstream of the mixing device.

It is also conceivable that the storage container itself forms the mixing device or a part of the mixing device, i.e. that the mixing takes place in the storage container itself. This is the case when one or more ingredients or the concentrate or concentrates are already present in the storage container and/or when the storage container has one or more connectors to which one or more dialysis concentrate containers are connectable or connected.

It is also conceivable that a line leads away from the storage container and serves the connection to the patient, with the line having a connector to which a dialysis concentrate container is connectable or connected. It can here be a glucose container or an electrolyte container, etc. In this case, the mixing device is formed by the line itself or by that part of the line in which the concentrate flowing out of the dialysis concentrate container meets the solution flowing through the line.

Provision is preferably made that a sterile filter is arranged in the line that leads to the port to the patient.

It is conceivable that the connector or connectors has/have a screw connection by means of which the dialysis concentrate container(s) is/are connectable.

It is alternatively or additionally conceivable that the connector has a membrane and a spike for piercing the membrane when establishing the connection on the connecting of the dialysis concentrate container. The fixing relative to one another of the two parts connected to one another can in this case likewise take place by a screw connection or also by a latch connection, by a bayonet connector, etc.

Provision is made in a further embodiment of the invention that a line leads away from the storage container and serves for connection to the patient, with the line being connected to a mixing container. In this case, the RO water or the solution containing RO water flows through the line into the mixing container and is mixed with one or more concentrates, etc. therein.

The dialysis concentrate or concentrates can, for example, be an osmotic agent, in particular glucose and/or electrolytes.

It is conceivable that a plurality of dialyzate concentrate containers are arranged behind one another. This means that a concentrate flows from one concentrate container into a further concentrate container and both concentrates are then mixed with the RO water or with the solution containing RO water.

The storage container is preferably formed by a tank or the storage container comprises a tank with provision preferably being made that the tank is partly or completely formed with rigid walls.

To be able to ensure the sterility of the storage container in a particularly reliable manner, the storage container is preferably formed by a bag or comprises a bag, with the bag preferably consisting of or comprising a flexible and/or elastic film. This bag can be discarded or sterilized or replaced with a new sterile bag after the treatment.

The existing high demands on sterility can also be satisfied when the storage container comprises a tank, preferably having one or more rigid walls, and a bag, with the bag being received in the tank and with the bag preferably being dimensioned such that it contacts one or more inner sides of the tank in the filled state. The flexible or elastic film of the bag can therefore be dimensioned such that it partly or completely fills the preferably rigid tank structure, i.e. such that it directly contacts the inner side of the wall of the tank.

Further measures for maintaining the sterility can comprise a UV irradiation. The sterilization means can thus in particular be a UV irradiation device by means of which the inner side of the storage container can be sterilized.

In a preferred embodiment of the invention, the storage container has a volume capacity in the range from 5 to 100 l, preferably in the range from 10 to 50 l.

The present invention further relates to a dialysis machine, in particular to a peritoneal dialysis machine, having a device for preparing dialysis solution, wherein the device has an RO system equipped with a filter for the provision of RO water and has a mixing device that is configured to mix a dialysis concentrate with the RO water, wherein a control device is provided that is configured to operate the RO system continuously, and wherein the control device is configured to operate the RO system with a smaller throughput when the dialysis machine is not in use and to operate it with a higher throughput when the dialysis machine is in use. A long-term operation of the RO system can also be ensured in this embodiment of the invention, with the throughput through the RO system being adapted to the current requirements, i.e. with it being made dependent on whether a treatment is carried out by means of the dialysis machine or not or on whether dialysis solution is required or not.

The dialysis machine in accordance with this embodiment of the invention can have one or more features characterized as follows: characterized in that the mixing device is connected downstream of the storage container, or in that the storage container itself forms the mixing device or a part of the mixing device; characterized in that the storage container contains dialysis concentrate, or in that the storage container is configured such that dialysis concentrate can be received in it, and/or in that the storage container has a connector to which a dialysis concentrate container is connectable or connected; characterized in that a line leads away from the storage container that serves the connection to the patient, with the line having a connector to which a dialysis concentrate container is connectable or connected; characterized in that the connector has a screw connection by means of which the dialysis concentrate container is connectable, and/or in that the connector has a membrane and a spike for piercing the membrane on the establishing of the connection when connecting the dialysis concentrate container; characterized in that a line leads away from the storage container that serves the connection to the patient, with the line preferably being connected to a mixing container; characterized in that a sterile filter is arranged in the line that serves the connection to the patient; characterized in that the dialysis concentrate is an osmotic agent, in particular glucose and/or electrolytes; characterized in that a plurality of dialysis concentrate containers are arranged behind one another; characterized in that the storage container is formed by a tank or comprises a tank, with provision preferably being made that the tank is partly or fully configured with rigid walls; characterized in that the storage container is formed by a bag or comprises a bag, with the bag preferably consisting of or comprising a flexible and/or elastic film; characterized in that the storage container comprises a tank and a bag, with the bag being received in the tank and with the bag preferably being dimensioned such that it contacts the inner sides of the tank in the filled state; characterized in that sterilization means, in particular a UV irradiation device, are provided by means of which the inner side of the storage container can be sterilized; and characterized in that the storage container has a volume capacity from 5-100 l, preferably from 10-50 l.

The dialysis machine in accordance with the invention is preferably a home dialysis machine, preferably a home peritoneal dialysis machine, i.e. a dialysis machine that is preferably used at the patient's home.

It is also conceivable that it is a dialysis machine, preferably a peritoneal dialysis machine, that is used in a mobile treatment device such as in a truck, a bus or the like, with the mobile treatment device having one or more dialysis machines by means of which patients can be treated in the mobile treatment device. The mobile treatment device can be any desired engine-operated land, water or air vehicle.

The present invention furthermore relates to a method of providing a dialysis solution in a dialysis machine in accordance with the instant invention, wherein the RO plant is continuously in operation. The RO system can here be controlled such that the throughput of the RO system is independent of whether a treatment is carried out by means of a dialysis machine or, alternatively thereto, can be controlled such that the throughput of the RO system is dependent on whether a treatment is carried out by means of the dialysis machine.

It is pointed out at this point that the terms "a" and "one" do not necessarily refer to exactly one of the elements, even though this represents a possible embodiment, but can also designate a plurality of elements. The use of the plural equally also includes the presence of the element in question in the singular and, conversely, the singular also includes a plurality of the elements in question.

Figure 2A:
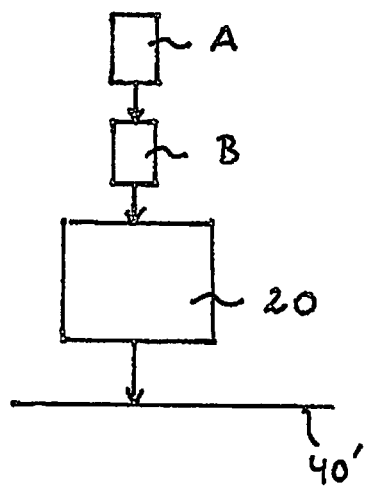
Figure 2B:
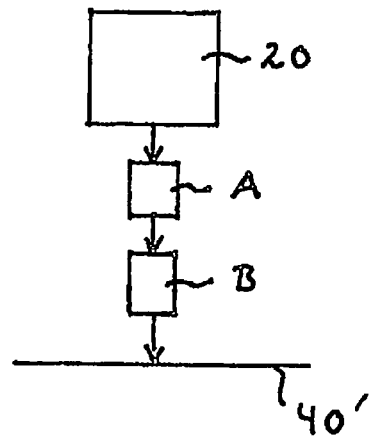
Figure 3:
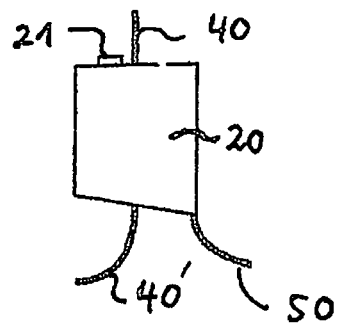

Further details and advantages of the invention will be explained in more detail with reference to an embodiment shown in the drawing:

There are shown:

FIG. 1: a schematic view of a peritoneal dialysis machine in accordance with the invention;

FIGS. 2A and 2B: different arrangements of dialysis concentrate containers relative to a mixing container; and FIG. 3: a schematic view of the storage container of a dialysis machine in accordance with the invention.

FIG. 1 shows by reference numeral 100 a PD machine in accordance with the invention in a schematic representation.

An RO system is marked by reference numeral 10 that is e.g. supplied with mains water through a filling connector, not shown. The RO system preferably comprises one or more pumps, filters, membranes, etc. that are not shown in the Figure.

RO water is prepared by reverse osmosis in the system 10 and is transferred from it by means of the line 40 and a pump, not shown, into the storage container 20.

As can be seen from FIG. 3, the storage container 20 is connected to an inflow line 40 from the RO system 10 and to an outflow line 40' that leads to the patient marked by reference symbol P in FIG. 1.

Reference numeral 50 in FIG. 3 marks a drain line by means of which the RO water or a solution containing RO water in the storage container 20 can be conducted into a drain. This takes place when the filling level in the store 20 has exceeded a specific value and the RO water is not required to prepare dialysis solution. The control of the fluid flows takes place by valves, not shown, that are preferably likewise controlled by the control device.

The RO system 10 is operated continuously. RO water is thus always available that first moves into the storage container 20.

The storage container 20 can be designed as a tank having rigid walls in which a replaceable bag is located into which RO water is conducted so that it only comes into contact with the bag, but not with the tank itself. It can thus be achieved by the use of a sterile bag that the RO water always remains sterile in the container 20. The demands on the sterility of the tank itself can thus be lower.

A concentrate (solid or liquid) can be located in the container 20, i.e. e.g. in the bag. It can e.g. be electrolytes. The case is generally also covered by the invention that there is no concentrate, but only RO water, in the container 20.

By introducing RO water through the line 40 from the RO system into the storage container 20, the RO water is mixed with concentrate located therein and the ready-to-use or substantially ready-to-use dialysis solution is prepared in this manner and is transported to the patient by means of the line 40'.

The storage container 20 thus not only serves as a store for receiving RO water in this case, but also as a mixing device for mixing RO water with concentrate(s).

However, the case not shown in the Figures is also covered by the invention that a mixing device, e.g. in the form of a further container in which the mixing of RO water and the concentrate or concentrates takes place, is arranged downstream of the storage container 20. This container can have one or more concentrates or one or more connectors for concentrates.

A glucose bag or glucose container that, as can be seen from FIG. 1, opens into the patient line 40' is shown by reference numeral 30. A valve, a pump or the like is preferably provided by means of which glucose and/or other concentrates such as electrolyte concentrates individual to the patient can be added as required via the control device.

Reference numeral 30 is thus representative of any desired container (rigid (e.g. a cartridge) or flexible (e.g. a bag)) that contains one or more concentrates in a solid and/or liquid form.

The dialysis machine 100 furthermore comprises the already named control device, not shown, (that can optionally also carry out a regulation), with the control device being designed to operate the components of the machine. The control device is here configured such that the RO system is also operated continuously when no dialysis solution is actually required. This can be achieved, for example, in that a pump that conveys water to or through the RO system is always in operation, i.e. also when no dialysis solution is required per se.

This has the advantage that the filter of the RO system is flushed continuously and not only intermittently, which reduces the probability for the occurrence of contamination. This is e.g. achieved by the continuous operation of a pump that is correspondingly controlled by the control device.

The pump or other device (e.g. a valve) can be controlled or configured such that the throughput through the RO system is always constant in time. It is, however, also conceivable to carry out the control in dependence on whether dialysis solution is required or not. In the latter case, the pump. etc. can be operated at a lower conveying power than in the first case.

If no dialysis solution is required over a longer time period, the RO water prepared in the RO system 10 is discarded via the drain 50 (cf. FIG. 3).

FIGS. 2A and 2B show further variants of the arrangement of concentrate containers that are marked by reference symbols A and B in FIG. 3.

A can, for example, be a glucose concentrate and B can be an electrolyte concentrate or vice versa.

FIG. 2A shows the case that the concentrates flow into the storage container 20; FIG. 2B shows the reverse arrangement in which the content of the storage container 20 successively flows through the concentrate containers A and B.

In both cases, the preferably ready-to-use solution moves into the line 40' that leads to the patient.

A connector that is connectable to a connector of the patient catheter in a fluid-tight manner is arranged at the end of the line at the patient side. The patient catheter is a hose section that is fixedly connected to the patient and leads into the peritoneum of the patient.

The dialysis machine can have one or more pumps, flow rate sensors, other sensors, clamps, valves, etc. that are not shown in the Figures.

The dialysis machine is preferably designed such that the patient only has to connect the patient catheter to the line 40' and the dialysis machine starts.

One or more of the functions of the dialysis machine can be arranged in a module or in a cassette that the user connects to the dialysis machine.

The invention claimed is:

1. A peritoneal dialysis machine having a device for preparing dialysis solution, wherein the device has a reverse osmosis (RO) system equipped with a filter for provision of RO water and has a mixing device that is configured to mix a dialysis concentrate with the RO water or with a solution containing the RO water, wherein a control device is provided that is configured to operate the RO system continuously, wherein a storage container is provided that is connected downstream of the RO system and that is configured to store the RO water generated in the RO system, and wherein the control device is configured to operate the RO system with a smaller throughput when no dialysis treatment is taking place and to operate it with a higher throughput when dialysis treatment is taking place.

2. A peritoneal dialysis machine in accordance with claim 1, characterized in that the mixing device is connected downstream of the storage container.

3. A peritoneal dialysis machine in accordance with claim 1, characterized in that the storage container contains dialysis concentrate; or in that the storage container is configured such that dialysis concentrate can be received in it; and/or in that the storage container has a connector to which a dialysis concentrate container is connectable or connected.

4. A peritoneal dialysis machine in accordance with claim 3, characterized in that the connector has a screw connection by means of which the dialysis concentrate container is connectable; and/or in that the connector has a membrane and a spike for piercing the membrane to establish a connection when connecting the dialysis concentrate container.

5. A peritoneal dialysis machine in accordance with claim 1, characterized in that a line leads away from the storage container and serves as a connection to a patient, the line having a connector to which a dialysis concentrate container is connectable or connected.

6. A peritoneal dialysis machine in accordance with claim 1, characterized in that a line leads away from the storage container and serves as a connection to a patient.

7. A dialysis machine in accordance with claim 6, characterized in that the line is connected to a mixing container.

8. A peritoneal dialysis machine in accordance with claim 6, characterized in that a sterile filter is arranged in the line that serves as the connection to the patient.

9. A peritoneal dialysis machine in accordance with claim 1, characterized in that the dialysis concentrate is glucose and/or electrolytes.

10. A peritoneal dialysis machine in accordance with claim 1, characterized in that a plurality of dialysis concentrate containers are arranged behind one another.

11. A peritoneal dialysis machine in accordance with claim 1, characterized in that the storage container is formed by a tank or comprises a tank.

12. A dialysis machine in accordance with claim 11, characterized in that the tank is partly or fully configured with rigid walls.

13. A peritoneal dialysis machine in accordance with claim 1, characterized in that the storage container is formed by a bag or comprises a bag.

14. A dialysis machine in accordance with claim 13, characterized in that the bag consists of or comprises a flexible and/or elastic film.

15. A peritoneal dialysis machine in accordance with claim 1, characterized in that the storage container comprises a tank and a bag, with the bag being received in the tank.

16. A dialysis machine in accordance with claim 15, characterized in that the bag is dimensioned such that it contacts inner sides of the tank in a filled state.

17. A peritoneal dialysis machine in accordance with claim 1, characterized in that a UV irradiation device is provided by means of which an inner side of the storage container can be sterilized.

18. A peritoneal dialysis machine in accordance with claim 1, characterized in that the storage container has a volume capacity from 5-100 liters.

19. A method of providing a peritoneal dialysis solution in a dialysis machine in accordance with claim 1, wherein the RO system is continuously in operation.

20. A method in accordance with claim 19, characterized in that the RO system can be controlled such that the throughput of the RO system is independent of whether a treatment is carried out by means of the peritoneal dialysis machine or, alternatively thereto, can be controlled such that the throughput of the RO system is dependent on whether a treatment is carried out by means of the peritoneal dialysis machine.

21. A peritoneal dialysis machine in accordance with claim 1, characterized in that the storage container has a volume capacity from 10-50 liters.

* * * * *